United States Patent [19]

Contessa et al.

[11] Patent Number: 5,423,953
[45] Date of Patent: Jun. 13, 1995

[54] PROCESS FOR RECOVERING COLUMN BOTTOM RESIDUES PRODUCED BY FRACTIONAL DISTILLATION OF ETHYLENE GLYCOL

[75] Inventors: Socrate Contessa, Salerno; Riccardo Tesser, Recale; Salvatore Barrella, Brusciano, all of Italy

[73] Assignee: Montefibre S.p.A., Milan, Italy

[21] Appl. No.: 188,207

[22] Filed: Jan. 27, 1994

[30] Foreign Application Priority Data

Feb. 5, 1993 [IT] Italy ............................ MI93A0198

[51] Int. Cl.⁶ .......................................... B01D 3/34
[52] U.S. Cl. ...................................... 203/38; 203/60; 203/71; 203/91; 568/871
[58] Field of Search .................. 203/60, 71, 91, 38, 203/73; 568/913, 871

[56] References Cited

U.S. PATENT DOCUMENTS

| | | | |
|---|---|---|---|
| 2,793,235 | 5/1957 | Jenkinson | 203/42 |
| 3,311,544 | 3/1967 | Riehl et al. | 203/53 |
| 3,367,847 | 2/1968 | Pierson | 203/81 |
| 4,732,653 | 3/1988 | Berg et al. | 203/60 |

OTHER PUBLICATIONS

Database WPI, Week 7937, Derwent Publications Ltd., London BGB, JP 54015812 (abstract).

*Primary Examiner*—Virginia Manoharan
*Attorney, Agent, or Firm*—Rogers & Wells

[57] ABSTRACT

A process for recovering column bottom residues produced by distillation of ethylene glycol resulting from an aromatic polyester production process, involving treating the residues with an aromatic mono-alkyl ester and distilling the reaction product.

11 Claims, No Drawings

PROCESS FOR RECOVERING COLUMN BOTTOM RESIDUES PRODUCED BY FRACTIONAL DISTILLATION OF ETHYLENE GLYCOL

This invention relates to a process for recovering column bottom residues produced by fractional distillation of the excess ethylene glycol resulting from the production of an aromatic polyester based on this glycol.

The process of the present invention is particularly directed towards the recovery of materials generally seen as waste byproducts to be incinerated without energy recovery or deposited in protected dumps.

Most of the processes for producing ethylene glycol-based aromatic polyesters, whether starting from aromatic diacids such as terephthalic acid (TPA) or from their esters such as dimethylterephthalate (DMT), are known to comprise two successive steps, namely:

i) production of the prepolymer by condensing the diacid or its diester with ethylene glycol; and
ii) production of the aromatic polyester by polycondensation of the prepolymer, with release of glycol or water, in the presence of a catalyst under increased temperature and high vacuum conditions. One of the most widely used catalysts is antimony trioxide.

The excess ethylene glycol recovered during the second step it), representing about 50% of that fed during the first step i), is recovered generally by distillation.

This recovered ethylene glycol is however impure because of the presence, inter alia, of diethyleneglycol (DEG), low molecular weight polyester chains (oligomers), antimony oxide, antimony bound to the oligomers, aromatic acids, their esters, various light ethylene glycol degradation products such as dioxane, methyl cellosolve and 1,3-methyl-dioxolane, methanol and water.

The aforesaid steps and excess ethylene glycol recovery processes are described, for example, in U.S. Pat. Nos. 2,778,373, 2,793,235 and 3,311,544.

A typical column bottom residue composition, comprising water and small quantities of sodium or potassium hydroxide added to neutralize the acidity of the crude glycol, is the following:

Antimony (as metal): 0.4–0.6%
Sodium (as metal): 0.6–1%
Diethylene glycol: 15–20%
Oligomers: 50–70%
Residual ethylene glycol: 20–30%.

The disposal of this distillation residue represents a considerable problem. In this respect, all known and suggested methods, such as incineration and storage in dumps, have various drawbacks.

Of these, incineration has the drawback of being costly by virtue of having to be conducted in furnaces authorized by the competent authorities as the material is toxic-noxious because of the presence of ethylene glycol in a quantity exceeding 5% by weight. In addition the raw materials are not recovered.

Storage requires the use of dumps suitable for toxic-noxious industrial refuse, the cost incurred being so high as to be unacceptable as an industrial solution. In addition, the ever increasing severity of environmental legislation makes such disposal unachievable.

Chemical treatment of column bottom residues in aromatic polyester production has been proposed. However none of the known processes has given industrially acceptable results as they are very costly and complicated in terms of investment and operation, and in addition it is very difficult to obtain the raw materials at a purity suitable for their use in the production of fibre-quality polyesters.

The proposed known chemical methods include:

a) methanolysis with recovery of the aromatic diacid dimethylester and ethylene glycol, as described in UK patents Nos. 1,458,486 and 2,041,916, and U.S. Pat. Nos. 3,907,868, 4,163,860, 3,776,945 and 3,321,510;
b) hydrolysis as described in UK patent 2,123,403; and
c) alkaline hydrolysis and precipitation of the aromatic diacid, as described in U.S. Pat. No. 4,013,519 and GDR patent 96,966.

All the known chemical methods also suffer from the problem of disposal of sodium, antimony and high-boiling degradation products, which represent 2–3 wt % of the initial material subjected to treatment.

Ethylene glycol could also be recovered from the distillation residue as such by further fractional distillation, but if the free ethylene glycol content falls below 5–10 wt % of the material, a crosslinked thermosetting product forms which is complicated and costly to handle.

An object of the present invention is to overcome the aforesaid drawbacks.

A more specific object of the present invention is to provide a process which enables the excess ethylene glycol used in aromatic polyester production to be totally recovered, without the aforesaid problems occurring.

In its most general aspect, the present invention attains these and further objects by treating the column bottom residue of ethylene glycol fractional distillation with a monofunctional reactive compound and distilling the resultant reaction product. The present invention therefore provides a process for recovering column bottom residues produced by distilling the excess ethylene glycol resulting from aromatic polyester production, consisting of:

A) adding to the column bottom residue an aromatic monoalkylester of formula (I):

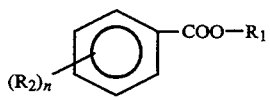

where $R_1$ is a $C_1$–$C_4$ alkyl radical, $R_2$ is a hydrogen atom or a $C_1$–$C_4$ alkyl radical and n is a whole number between 1 and 5, in a quantity such that the ratio of aromatic mono-alkyl ester equivalents to glycol —OH equivalents of the free glycols in the residue is at least 0.1;
B) gradually heating the reaction mixture to about 200°–220° C. so distilling off the alcohol which forms; and
C) applying a vacuum not exceeding 5000 Pa while maintaining the temperature constant, and distilling off the ethylene glycol and unreacted aromatic mono-alkyl ester of formula (I).

The process of the present invention not only enables substantially the whole of the free ethylene glycol to be recovered, its quantity being reduced to less than 0.5% of the final product obtained, without formation of a crosslinked thermosetting by-product, but also enables the column bottom residue of ethylene glycol distillation to be converted from toxic-noxious industrial refuse into special industrial refuse, and hence no longer subject to the restrictions posed by European legislation for toxic-noxious products. The column bottom residue treated by the process of the present invention can be usefully used as an alternative fuel, for example in cement works, or for the production of plasticizers for polyolefins by solvent extraction.

The column bottom residue from ethylene glycol distillation can either be treated once by the process of the present invention or, preferably, be treated two or more times using the same stage sequence A), B) and C).

If the treatment is repeated two or more times, the quantity of aromatic mono-alkyl ester of formula (I) added to each stage A) of the process is preferably increased progressively with respect to the free glycol —OH equivalents present in the residue to be treated; in addition the glycol distillation in the intermediate treatments can be effected under milder vacuum conditions.

For example, if only one treatment is used, the quantity of aromatic mono-alkyl ester of formula (I) added in stage A) is such that the ratio of aromatic mono-alkyl ester equivalents to free glycol —OH equivalents is between 0.15 and 1 and preferably between 0.2 and 0.5, and the glycol distillation in stage C) is effected at a pressure not greater than 5000 Pa and preferably between 100 and 1000 Pa.

If however the treatment is repeated several times, the quantity of aromatic mono-alkyl ester of formula (I) added in stage A) of the initial treatment is equal to the aforestated, whereas that added in each stage A) of the subsequent treatments is increased progressively. In addition, the ethylene glycol distillation in stage C) of each intermediate treatment can be conducted under milder conditions, for example at a pressure not exceeding 5000 Pa and preferably between 5000 and 100 Pa.

In particular, the quantity of aromatic mono-alkyl ester added in stage A) of the second treatment is preferably such that the ratio of aromatic mono-alkyl ester equivalents to free glycol —OH equivalents in the residue to be treated is between 1 and 2. If a further treatment is effected, the quantity of aromatic mono-alkyl ester added can be further increased to achieve a ratio of aromatic mono-alkyl ester equivalents to free glycol —OH equivalents in the residue to be treated which can be greater than 2 and up to 5.

If the process of the present invention is effected in two or more successive treatments, the residual ethylene glycol quantity in the treated material is substantially negligible, being less than 0.1% by weight.

Any aromatic mono-alkyl ester of the aforesaid formula (I) can be used in the process of the present invention. Particularly interesting results are obtained if $R_1$ is a methyl or ethyl radical and $R_2$ is hydrogen or methyl.

Examples of aromatic mono-alkyl esters of formula (I) which can be used in the process of the present invention include methyl benzoate, ethyl benzoate, methyl p-toluate, ethyl p-toluate etc. Methyl benzoate is particularly preferred because of its industrial availability, it being a by-product of dimethylterephthalate production. A typical by-product of dimethylterephthalate production comprises 95 wt % of methyl benzoate, 3 wt % of methyl p-toluate and 2 wt % of miscellaneous impurities.

The time during which the reaction mixture of stage A) is heated to achieve the temperature of about 200°–220° C. is not critical, and is generally between 30 minutes and 2 hours. Heating is continued at atmospheric pressure until the alcohol which forms has been completely removed. Vacuum is then applied to reduce the pressure within the reactor to the desired value. Under these conditions, the ethylene glycol, diethylene glycol and the unreacted aromatic mono-alkyl ester of formula (I) added during stage A) distil off and are recovered.

The product obtained after single or multiple treatment by the process of the present invention has an ethylene glycol content of less than 0.5 wt % and possibly less than 0.1 wt %, a melting point of less than 100° C. and an absolute viscosity of less than 200 cps at 120° C. and 100 cps at 140° C. This product can be used as an alternative fuel (providing 5000–6000 kCal/kg) or be solvent-extracted to recover ethylene glycol benzoate, diethylene glycol benzoate and hydroxyethylterephthalate, used as polyolefin plasticizers.

Some illustrative but non-limitative examples of the present invention are reported hereinafter to improve its understanding and aid its practical implementation.

In the examples, the ethylene glycol and diethylene glycol quantities were determined by gas chromatography analysis and the metal quantity by atomic absorption analysis using a Perkin Elmer spectrometer.

EXAMPLE 1

The following were fed into a 1 liter reactor fitted with a Vigreux fractional distillation column, thermostat and high-vacuum pump:

380 g of methyl benzoate and 600 g of column bottom residue from ethylene glycol distillation, having the following wt % composition:

| | |
|---|---|
| Ethylene glycol | 30 |
| Diethylene glycol | 10 |
| Oligomers | 40 |
| | (as TPA equivalents) |
| Antimony | 0.2 |
| Sodium | 0.25 |
| impurities | to 100. |

The ratio of methyl benzoate equivalents to free glycol —OH equivalents was about 0.5.

The mixture temperature was raised to 200° C. under atmospheric pressure over two hours, the methanol distilling off (about 80 g). On termination of distillation vacuum was applied gradually to 200 Pa over 40 minutes, the temperature being maintained constant and the distillation products being distilled off and recovered. 130 g of ethylene glycol, 20 g of diethylene glycol and 40 g of unreacted methyl benzoate were obtained.

The bottom product obtained in this manner had a melting point of 80° C., a viscosity of 100 cps at 120° C. and 80 cps at 140° C., and the following wt % composition:

| | |
|---|---|
| Methyl benzoate | 5 |
| Free ethylene glycol | 0.3 |
| Ethylene and diethylene glycol benzoate | 40 |
| Oligomers with terminal benzene ring | to 100. |

EXAMPLE 2

The following were fed into the reactor of Example 1:
- 130 g of methyl benzoate and
- 661 g of column bottom from ethylene glycol distillation having the composition of Example 1.

The ratio of methyl benzoate equivalents to free glycol —OH equivalents was 0.2.

The mixture temperature was raised to 200° C. under atmospheric pressure over two hours, the methanol distilling off (about 25 g). On termination of distillation vacuum was applied gradually to 1000 Pa over 40 minutes, the temperature being maintained constant. 160 g of distillate of the following composition were distilled off and recovered:

| | |
|---|---|
| Ethylene glycol | 75 wt % |
| Diethylene glycol | 13 wt % |
| Methyl benzoate | 12 wt %. |

141 g of methyl benzoate were added to the reactor (ratio of methyl benzoate equivalents to free glycol —OH equivalents: 1) and the methyl alcohol distilled off while maintaining the temperature constant at 200° C. under atmospheric pressure. On termination of distillation (9 g of methyl alcohol distilled off) vacuum was applied gradually to 200 Pa over 40 minutes, the temperature being maintained constant. 73 g of two-phase distillate (40+33) of the following overall composition were distilled off and recovered:

| | |
|---|---|
| Ethylene glycol | 15 wt % |
| Diethylene glycol | 6 wt % |
| Methyl benzoate | 79 wt %. |

The bottom product obtained in this manner had a me[t]ing point of 70° C., a viscosity of 150 cps at 120° C. and 90 cps at 140° C., and the following wt % composition:

| | |
|---|---|
| Methyl benzoate | 5 |
| Free ethylene glycol | <0.1 |
| Ethylene and diethylene glycol benzoate | 50 |
| Oligomers with terminal benzene ring | to 100. |

We claim:

1. A process for recovering column bottom residues produced by distilling excess ethylene glycol resulting from aromatic polyester production, consisting of:
   A) adding to the column bottom residue an aromatic mono-alkylester of formula (I):

where $R_1$ is a $C_1$–$C_4$ alkyl radical, $R_2$ is a hydrogen atom or a $C_1$–$C_4$ alkyl radical and n is a whole number between 1 and 5, in a quantity such that the ratio of aromatic mono-alkyl ester equivalents to glycol —OH equivalents of the free glycols in the residue is at least 0.1;
   B) gradually heating the reaction mixture to about 200°–220° C. to distil off the ethylene glycol which forms; and
   C) applying a vacuum not exceeding 5000 Pa while maintaining a constant temperature, and distilling off the ethylene glycol and unreacted aromatic mono-alkyl ester of formula (I).

2. A process as claimed in claim 1, wherein the quantity of aromatic mono-alkyl ester of formula (I) added in stage A) is such that the ratio of aromatic mono-alkyl ester equivalents to free glycol —OH equivalents is between 0.15 and 1.

3. A process as claimed in claim 2, wherein the ratio of equivalents of aromatic mono-alkyl ester of formula (I) to free glycol —OH equivalents is between 0.2 and 0.5.

4. A process as claimed in claim 1, wherein the glycol distillation in stage C) is effected at a pressure of between 100 and 1000 Pa.

5. A process as claimed in claim 1, wherein the aromatic mono-alkyl ester has the aforesaid formula (I) where $R_1$ is a methyl radical or ethyl radical and $R_2$ is hydrogen or methyl radical.

6. A process as claimed in claim 5, wherein the aromatic mono-alkyl ester of formula (I) is methyl benzoate.

7. A process as claimed in claim 1, wherein stages A), B) and C) are repeated at least twice.

8. A process as claimed in claim 7, wherein the quantity of aromatic mono-alkyl ester of formula (I) added during stage A) of the initial treatment is such that the ratio of aromatic mono-alkyl ester equivalents to free glycol —OH equivalents is between 0.15 and 1, whereas the quantity added during each stage A) of the subsequent treatments is increased progressively, the ethylene glycol distillation in stage C) of each intermediate treatment being affected at pressures of between 5000 and 100 Pa.

9. A process as claimed in claim 7, wherein the quantity of aromatic mono-alkyl ester added during the second treatment is such that the ratio of mono-alkyl ester equivalents to free glycol —OH equivalents in the residue to be treated is between 1 and 2.

10. A process as claimed in claim 7, wherein the quantity of aromatic mono-alkyl ester added during treatments subsequent to the second is such that the ratio of mono-alkyl ester equivalents to free glycol —OH equivalents in the residue to be treated is greater than 2 and as great as 5.

11. A process as claimed in claim 1, wherein the time during which the mixture of stage A) is heated to attain the temperature of 200°–220° C. is between 30 minutes and 2 hours, the heating being continued under atmospheric pressure until the ethylene glycol which forms has been completely removed.

* * * * *